United States Patent [19]

Gray et al.

[11] Patent Number: 5,084,448
[45] Date of Patent: Jan. 28, 1992

[54] FUNGICIDAL PHENYL AZOXIME COMPOSITIONS

[75] Inventors: Andrew C. G. Gray, London; William W. Wood; Thomas W. Naisby, both of Sittingbourne, all of England

[73] Assignee: Shell Research Limited, United Kingdom

[21] Appl. No.: 561,140

[22] Filed: Aug. 1, 1990

[30] Foreign Application Priority Data

Aug. 4, 1989 [GB] United Kingdom ............ 8917850

[51] Int. Cl.$^5$ ............ C07C 291/08; A01N 37/52; A01N 51/00
[52] U.S. Cl. ............ 514/149; 534/566; 534/567; 534/572
[58] Field of Search ............ 534/566, 567, 738; 514/149, 150

[56] References Cited

U.S. PATENT DOCUMENTS

| | | | |
|---|---|---|---|
| 2,426,313 | 8/1947 | Ludwig et al. | 534/567 |
| 4,425,271 | 1/1984 | Gutman | 534/738 |
| 4,981,954 | 1/1991 | Nakayama et al. | 534/766 |

OTHER PUBLICATIONS

Kalia et al., Chemical Abstracts, vol. 87, No. 38406w (1977).
Natarajan et al., Chemical Abstracts, vol. 100, No. 113933h (1984).
Shawali et al., Chemical Abstracts, vol. 86, No. 88976g (1977).

*Primary Examiner*—David B. Springer
*Assistant Examiner*—Fiona T. Powers

[57] ABSTRACT

Novel compounds of the general formula

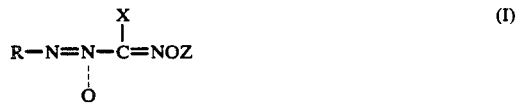

where R represents an optionally substituted aryl or heteroaryl group; X represents a hydrogen atom or an amino group or an optionally substituted alkyl, aryl or heteroaryl group; and Z represents a hydrogen atom or alkanoyl group; are fungicidal.

7 Claims, No Drawings

FUNGICIDAL PHENYL AZOXIME COMPOSITIONS

This invention relates to novel phenyl azoxime compounds, to their use as biocides, especially fungicides, to biocidal compositions containing such compounds, and to the preparation of the compounds.

The present invention is based upon the derivation of certain novel phenylaldoxime compounds, and derivatives thereof, and of the discovery of their activity in combating fungi, including plant pathogenic fungi. The compounds are characterised by N-oxidation.

According to a first aspect of the present invention there is provided a compound of the general formula

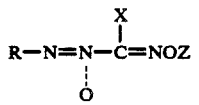
(I)

where R represents an optionally substituted aryl or heteroaryl group; X represents a hydrogen atom or an amino group or an optionally substituted alkyl, aryl or heteroaryl group; and Z represents a hydrogen atom or a group of formula —$COR^1$ where $R^1$ represents an optionally substituted alkyl group.

Unless otherwise specified in this specification, an alkyl group may be linear or branched and suitably contains up to 10, preferably up to 6, and most preferably up to 4, carbon atoms, preferred examples being methyl and ethyl.

A preferred optionally substituted aryl group is optionally substituted phenyl.

A heteroaryl group may be monocyclic or multicyclic. It may suitably contain 5 to 10 ring atoms, hetero atoms suitably being selected from nitrogen, oxygen and sulphur atoms, 1 to 4 ring atoms suitably being hetero atoms.

Unless otherwise stated in this specification, when any groups are designated as being optionally substituted, the substituent groups which are optionally present may be any of those customarily employed in the development of biocidal compounds, and/or the modification of such compounds to influence their structure/activity, persistence, penetration or other property. In relation to alkyl groups, specific examples of such substituents include halogen, especially fluorine, chlorine or bromine atoms, and phenyl, cyano, amino, hydroxy, alkoxy, (alkyl)amino and haloalkyl groups, In relation to an aryl or heteroaryl moiety, optional substituents include halogen atoms, for example fluorine, chlorine, bromine and iodine atoms, and nitro, cyano, amino, (alkyl)amino, (alkyl)amido, hydroxy, alkoxy, alkyl, alkoxycarbonyl and haloalkyl (e.g. $CF_3$) groups.

Preferably, R represents an optionally substituted phenyl group, optionally substituent(s) preferably being selected from halogen atom(s), nitro, alkyl and alkoxycarbonyl group(s). Particularly preferred is a phenyl or, especially, a halophenyl group, such a group preferably having halogen at the 4-position, and being optionally substituted elsewhere in the ring.

Preferably, X represents a hydrogen atom or an optionally substituted, preferably unsubstituted, alkyl, phenyl or a thienyl group. Preferably, X represents a hydrogen atom.

It should be noted that compounds of the general formula I may exist as cis or trans isomers, and that the scope of the present invention covers any such isomers, isolated or together.

It should also be noted that compounds of general formula I could be in any of the following forms:

(IA)

(IB)

(IC)

It is believed on the basis of NMR analysis, that form IA is the preferred/dominant form, rather than form IB or IC, but it should be noted that the scope of the present invention covers any such forms, and for this reason the oxygen atom is shown connected by a dotted bond in the compound of general formula I.

In accordance with a further aspect of the invention there is provided a method of combating a fungus at a locus, which comprises treating the locus with an effective amount of a compound of general formula I.

In the method of the invention the locus may be an agricultural or horticultural locus, for example plants subject to attack, seeds of such plants or the medium in which such plants are growing or are to be grown. Compounds of the present invention have been shown to exhibit activity against a range of important fungi, including vine downy mildew, vine grey mould, wheat leafspot, barley powdery mildew, tomato early blight, wheat eyespot, seedling wheat blight and wheat brown rust. Such a locus as mentioned above may suitably be treated with a compound I at an application rate in the range 0.05–4 Kg/ha, preferably 0.1–1 Kg/ha.

The invention further provides the use as a fungicide of a compound of the general formula I as defined in any of the above statements.

Nematicidal activity has also been found in compounds of general formula I and nematicidal use of the compounds constitutes a further aspect of the invention.

Further in accordance with the invention there is provided a fungicidal composition which comprises a carrier and, as active ingredient, a compound of general formula I, as defined above.

A carrier in a composition according to the invention is any material with which the active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating biocidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexenone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emusifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10% w of active ingredient. Granules are usually prepared to have a size between 10 and 100 BS mesh (1.676–0.152 mm), and may be manufactured by agglomeration or impregnation techniques. Generally, granules will contain 0.5–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick "mayonnaise"-like consistency.

The composition of the invention may also contain other ingredients, for example other compounds possessing herbicidal, insecticidal or fungicidal properties.

In accordance with a further aspect of the present invention there is provided a process for the preparation of a novel compound of general formula I, as defined in any preceding statement, which comprises treating a compound of the general formula

$$R-NH-N=C-COOH \quad \text{(II)}$$
with X above C.

where R and X are as defined above, but X is not an amino group, with a base and a nitrite salt, and oxidising the resultant product. Suitably, the nitrite reaction takes place in the presence of a solvent, for example water. The reaction is preferably effected at a temperature in the range 40° C. to the reflux temperature. The base may be, for example, sodium carbonate. The nitrite may be an alkali metal salt, for example sodium nitrite. Acidification completes the step. The product is a compound of formula I wherein Z is hydrogen.

The compound of general formula II may be prepared by reaction of a hydrazine of general formula

R—NH—NH$_2$ (III)

with a carboxylic acid of general formula X—C-(O)—COOH (V). This reaction suitably takes place in a solvent, for example water or an organic solvent, at a temperature in the range −20° to 50° C.

Further information on this method is available in Synth. Comm., 16(2), 163–167, 1968 (J. W. Lyga), and in J. Prakt. Chem., (2)75, 121, 1906, (M. Busch, E. Meussdorffer).

In accordance with a further aspect of the invention there is provided a process for the preparation of a compound of the general formula I, wherein X is as defined above, but is not a hydrogen atom or an amino group, which comprises treating a compound of the general formula

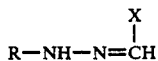

with a higher alkyl nitrite in the presence of a base; and oxidising the product. The reaction with the nitrite suitably takes place in an organic solvent, such as an alcohol, at a temperature in the range 40°-120° C., preferably under reflux. Suitable bases include alkali metal alkoxides. Particularly suitable base/solvent systems include sodium ethoxide/ethanol and sodium methoxide/methanol. Acidification completes the step. The product is a compound of formula I in which Z is hydrogen.

Further information on this method is obtainable in Berichte XXXVI, 85, 1903 (Bamberger, E., and Pemsel, W.) and in U.S. Pat. No. 4,425,271.

In accordance with a further aspect of the invention there is provided a process for the preparation of a compound of the general formula I, wherein X is a hydrogen atom, which comprises reaction of a diazonium compound of general formula $R-N_2^+X^-$ with malonic acid in the presence of a base, and of a nitrite salt, for example an alkali metal nitrite. Acidification completes the step, yielding the unoxidised product whereupon standard oxidation is carried out. The product is a compound of general formula I wherein Z is hydrogen. The reaction is suitably carried out in a solvent, for example water, at a temperature in the range $-10°$ to 20° C.

Further information on this method is available in Tetrahedron, 1977, 33(13), p. 1625-8 (Shawali, A. S. and Altahou, B. M.).

Novel compounds of general formula I wherein X represents an amino group may be prepared by treating a compound of general formula $R-N_2CN$ (suitably obtained by diazotisation of an aniline $R-NH_2$, followed by cyanuration) with hydroxylamine or an acid addition salt thereof, in the presence of a base, for example sodium hydroxide, followed by oxidation of the product. Acidification precipitates the product.

Further information on the above method is contained in Gazz. Chem. Ital., 63, 923-926, 1933 (G. Long).

Standard oxidation methods may be used, for example using a "peroxy" compound, for example hydrogen peroxide, or a peroxycarboxylic acid in a suitable inert organic solvent, for example a halogenated hydrocarbon, such as dichloromethane, at a temperature in the range, suitably, $-20°$ to 60° C. Suitable acids include peroxytrifluoroacetic acid and metachloroperbenzoic acid.

To prepare a compound of general formula I wherein Z represents a group of general formula $-COR^1$, a compound of general formula I, or its unoxidised precursor, where Z represents a hydrogen atom, is preferably reacted with an appropriate acid halide $R^1-CO-Hal$, (preferably chloride) in the presence of a base, for example dimethylaniline, pyridine, sodium hydroxide or triethylamine, in an inert organic solvent, such as an ether or alcohol, at a temperature in the range 0°-50° C.

The starting materials described herein are known or else may be prepared from known compounds by standard methods.

The invention will now be further illustrated by the following examples.

EXAMPLE 1

Preparation of Phenylazoacetaldoxime-N-oxide
(R = Phenyl; x = Methyl; Z = Hydrogen)

Acetaldehyde (30 g), in water (20 ml) and ethanol (120 ml), was treated with phenyl hydrazine (60 g), added in portions, with cooling. The reaction mixture was stirred at ambient temperature for about 2 hours until precipitation was complete. The phenylhydrazone product, $Ph-NH-N=CHCH_3$, was washed with a little aqueous ethanol, and dried. mp 95°-97° C. The phenylhydrazone (33 g) was added to sodium ethoxide (56 g sodium in 1 liter ethanol). Amyl nitrite (75 ml) was added and the reaction mixture was heated under reflux for about 1 hour. On cooling, the reaction mixture was poured into iced water (1.5 liter) containing 2M sodium hydroxide solution (250 ml). The solution was washed with diethyl ether to remove amyl nitrite, and the aqueous layer was acidified by addition of 2M hydrochloric acid, and extracted with diethyl ether. The diethyl ether was removed and the residue recrystallised from cyclohexane, yielding phenylazocetaldoxime (19.6g), mp 118°-120° C. The mother liquors were flash chromatographed on silica, eluted with dichloromethane, to give a further 6.7 g.

Analysis: Calc. %: C 58.9, H 5.5, N 25.8,
Found %: C 58.9, H 5.5, N 25.9.

The aldoxime (8.0 g; 0.05 mole) in $CH_2Cl_2$ (c. 100 ml) at $-10°$ C. was treated with peroxytrifluoroacetic acid (100 ml of 0.5M solution in $CH_2Cl_2$) for about 1 hour. The reaction mixture was washed with dilute sodium bicarbonate solution (c. 100 ml) and dried over $MgSO_4$. The solvent was removed under vacuum and the brown solid recrystallised from cyclohexane. Yield 4.1 g. mp 121° C. m/e 179.

Analysis: Calc. %: C 53.7, H 5.0, N 23.4,
Found %: C 53.7, H 5.1, N 23.3.

EXAMPLE 2

Preparation of 4-Chlorophenylazobenzaldoxime-N-oxide

Benzaldehyde phenylhydrazone (9.2 g; 0.04 mole) was added to sodium ethoxide (0.04 mole) in ethanol (100 ml). Amyl nitrite (12 ml; 0.09 mole) was added and the reaction mixture was refluxed for thirty minutes. The cooled reaction mixture was then poured into iced water (300 ml) containing 2M sodium hydroxide solution (40 ml). After washing with diethyl ether the aqueous layer was acidified with 2M sulphuric acid and extracted into diethyl ether. The solvent was removed and the product recrystallised from ethanol. Yield 5.4 g. mp 123° C. m/e found 259/261. The product was oxidised in analogous manner to that described in Example 1. mp 144° C. m/e 275/277.

Analysis: Calc. %: C 56.6, H 3.7, N 15.3,
Found %: C 55.8, H 3.7, N 15.0.

EXAMPLE 3

Preparation of 4-Nitrophenylformaldoxime-N-oxide p-Nitrophenylhydrazine (30.6 g; 0.2 mole) in water (200 ml) and concentrated hydrochloric acid (20 ml) was treated with glyoxylic acid (20 g; 0.2 mole) in water (40 ml). The immediate quantitive yield of hydrazone was filtered off and used directly in the next stage. The hydrazone (approx. 0.2 mole) was added to a solution of sodium carbonate (50 g; 0.5 mole) and sodium nitrite (26 g; 0.37 mole) in water (800 ml). The suspension was cooled to 0° C. and acidified by dropwise addition of glacial acetic acid. The reaction mixture was filtered, the solid obtained washed with water, and purified by flash chromatography using a silica column eluting with methylene dichloride. The yellow solid obtained was recrystallised with ethanol/water. Yield 11.2 g. mp 158°–160° C. m/e 194.

The product was oxidised in analogous manner to that described in Example 1, to yield the title compound. mp 163°–165° C. m/e 210

Analysis: Calc. %: C 40.0, H 2.9, N 26.7,
Found %: C 40.6, H 3.2, N 26.6.

EXAMPLE 4

Preparation of 4-Chlorophenylformaldoxime-N-oxide p-Chloroaniline (25.5 g; 0.2 mole) in 50% aqueous hydrochloric acid solution (100 ml) was diazotised by the dropwise addition of sodium nitrite (14 g; 0.2 mole) in water (80 ml) at 0° C. This was added dropwise, also at 0° C., to a cold solution of sodium acetate (16 g; 0.2 mole) and glacial acetic acid (24 ml; 0.4M) in water (80 ml). The prepared solution was then added dropwise, at 0° C., to a stirred solution of malonic acid (20.8 g; 0.2 mole), potassium hydroxide (30 g; 0.53 mole) and sodium nitrite (16 g; 0.23 mole) in water (400 ml). The reaction mixture was allowed to stand overnight at 4° C. The dark red solid obtained was filtered off, in dissolved methylene dichloride and extracted with 10% aqueous sodium carbonate solution (4×200 ml). The basic later was then acidified with 2M sulphuric acid and the yellow precipitate filtered off and recrystallised from methanol/water.

Yield 5.6 g. mp 140° C. m/e 183/185. The product of the preceding steps was oxidised in analogous manner to that described in Example 1, to yield the title compound. mp 151°–153° C. m/e 199/201

Analysis: Calc. %: C 42.1, H 3.0, N 21.1,
Found %: C 42.9, H 2.5, N 21.3.

Further compounds were prepared according to procedures similar to those described in the preamble and in Examples 1 to 4. Data on these compounds are set out in Table 1 below. In Table 1, reference is made to a compound of the general formula R—N(O)=N—C(X-)=NOZ

EXAMPLE B1

The fungicidal activity of compounds of the invention was investigated by means of the following tests.

(a) Direct Protectant Activity against Vine Downy Mildew (*Plasmopara viticola*; Pvp)

The test is a direct protectant one, using a foliar spray. The lower surfaces of leaves of whole vine plants (cv Cabernet Sauvignon) are sprayed with a solution of active material in 1:1 v/v water/acetone containing 0.04% w "Triton X-155" (trade mark) (octylphenol polyoxyethylene surfactant), at a dosage of 1 kilogram of active material per hectare using a track sprayer which delivers 620 liters/ha, and after a subsequent 24 hours under normal glasshouse conditions the lower surfaces of the leaves are inoculated by spraying with an aqueous solution containing $10^4$ zoosporangia/ml. The inoculated plants are kept for 24 hours in a high humidity compartment, 5 days under normal glasshouse conditions and then returned for a further 24 hours to high humidity. Assessment is based on the percentage of leaf area covered by sporulation compared with that on control leaves.

(b) Direct Protectant Activity against Vine Grey Mould (*Botrytis cinerea*; Bcp)

The test is a direct protectant one using a foliar spray and is effected as described under (a), with the difference that the leaves are inoculated by spraying with an aqueous solution containing $10^5$ conidia/ml.

(c) Activity against Wheat Eyespot (*Pseudocereosporella herpotrichoides*; Ph).

The test is an in vitro one. Samples are prepared wherein 0.7 mls solution containing 2 mg active material dissolved in acetone is evenly dispersed in 20 ml molten half-strength potato dextrose agar (formed by dissolving 2 g potato extract, 10 g dextrose and 7.5 g agar in 1 liter of water and sterilising for 15 minutes at 121° C.) and the resulting 20 ml portions are allowed to set in 9 cm petri dishes. The concentration of active material in the resulting samples is 100 ppm. Upon setting, two plugs of 5 mm diameter taken from the advancing edge of a stock plate of a 3 to 4 week old culture of *P. herpotrichoides* on full strength potato dextrose

TABLE 1

| Compound of Example No. | R | X | Z | Analysis CHN Calc. % Found % | | | mp/bp (°C.) | m/e |
|---|---|---|---|---|---|---|---|---|
| 5 | 4-CL-Ph | $CH_3$ | H | 45.0 / 45.3 | 3.8 / 3.9 | 19.6 / 19.5 | 150–153 | 213/215 |
| 6 | 4-F-Ph | 2-thienyl | H | 49.8 / 49.8 | 3.0 / 3.1 | 15.8 / 15.7 | 175–177 | 265 |
| 7 | Ph | H | H | 50.9 / 51.3 | 4.3 / 4.4 | 25.5 / 25.5 | 74–76 | 165 |
| 8 | Ph | Ph | H | 64.8 / 65.2 | 4.6 / 4.7 | 17.4 / 17.3 | 122–124 | 241 |
| 9 | Ph | 2-thienyl | H | 53.4 / 53.5 | 3.7 / 3.7 | 17.0 / 17.0 | 154–155 | 247 |
| 10 | 4-Br-Ph | H | H | 34.5 / 34.7 | 2.5 / 2.5 | 17.2 / 17.0 | 149–150 | 244 |
| 11 | 4-$COOC_2H_5$-Ph | H | H | 51.6 / 52.1 | 5.3 / 5.3 | 20.1 / 20.3 | 113–115 | 209 |
| 12 | 2-F-Ph | H | H | 50.3 / 51.9 | 3.6 / 4.0 | 25.1 / 24.8 | 134–136 | 167 |
| 13 | 4-$^t$Bu-Ph | H | H | 59.7 / 59.1 | 6.8 / 6.7 | 19.0 / 18.6 | 124–126 | 221 |
| 14 | 4-$CH_3$-Ph | H | H | 53.7 / 54.6 | 5.1 / 5.1 | 23.5 / 23.6 | 115–117 | 179 | agar, incubated at 20°–22° C. in darkness, are placed, equally spaced on the surface of each sample, mycelial side uppermost. The samples are incubated for 11 days at 20°–22° C. in darkness before assessment. Diametric growth is measured with the width of the plug subtracted and results compared with growth on a sample wherein 0.7 ml acetone containing no active material is dispersed in 20 ml half-strength potato agar.

(d) Activity against Seedling Wheat Blight (*Fusarium culmorium*; Fs)

The test is an anti-sporulant one using a soil drench. Surface sterilised wheat seeds (var Waggoner) are inoculated by soaking in an aqueous suspension containing $7 \times 10^5$ spores/ml (60 mg seed per 80 ml suspension) at 22° C. for 6 hours. The seeds are then sown in pots (5 per pot) in sand at a depth of 1 cm. 1 day after inoculation and planting the active material is applied at a rate of 10 kg/ha by pouring on a soil drench (concentration 0.36 g/l active material in 12% v/v acetone/water) evenly over the sand. The pots are then transferred to glasshouse, kept at 25° C. and watered sparingly. 21 days after inoculation the resulting seedlings are removed from the pots and their roots are gently washed. Visual assessment is made based on lesion development on stem base and upper roots in comparison with control seedlings.

(e) Activity against Wheat Leafspot (*Leptosphaeria nodorum*; Ln)

The test is a direct antisporulant one, using a foliar spray. Leaves of wheat plants (cv Mardler), at the single leaf stage, are inoculated by spraying with an aqueous suspension containing $8 \times 10^5$ spores/ml. The inoculated plants are kept for 24 hours in a high humidity compartment prior to treatment. The plants are sprayed at a dosage of 1 kg. of active material per hectare using a track sprayer as described under (a). After drying, the plants are kept for 5 days under normal glasshouse conditions, followed by assessment. Assessment is based on the percentage of leaf area covered by sporulation compared with that on leaves of control plants.

(f) Activity against Barley Powdery Mildew (*Erysiphe graminis* f.sp. *hordei*; Eg)

The test is a direct antisporulant one, using a foliar spray. Leaves of barley seedlings, cultivar Golden Promise, are inoculated by dusting with mildew conidia one day prior to treatment with the test compound. The inoculated plants are kept overnight at glasshouse ambient temperature and humidity prior to treatment. The plants are sprayed at a dosage of 1 kg. of active material per hectare using a track sprayer as described under (a). After drying, plants are returned to a compartment at ambient temperature and humidity for up to 7 days, followed by assessment. Assessment is based on the percentage of leaf area covered by sporulation compared with that on leaves of control plants.

(g) Activity against Tomato Early Blight (*Alternaria solani*; As)

The test is a direct protectant one using a foliar spray. The upper surfaces of leaves of young tomato plants are sprayed with a solution of active material as described in (a) above. After 24 hours under normal glasshouse conditions, the upper surfaces of the leaves are inoculated by spraying with an aqueous suspension containing $10^4$ spores/ml. The inoculated plants are kept for 72 hours in a high humidity compartment and are then removed to lower humidity (50–70% relative humidity). Assessment is made 8 days after inoculation.

(h) Activity against Wheat Brown Rust *Puccinia recondita*; Pr)

The test is a direct protectant one using a foliar spray. Wheat seedlings (cv Brigand) are grown to the 1–1.5 leaf stage. The plants are then sprayed with the test compound at a dosage of 1 kg/ha using a track sprayer as described under (a). Test compounds are applied as solutions or suspensions in a mixture of acetone and water (50:50 $v/v$) containing 0.04% surfactant ("TWEEN 20"—Trade Mark).

18–24 hours after treatment, the seedlings are inoculated by spraying the plants from all sides with an aqueous spore suspension containing about $10^5$ spores/ml. For 18 hours after inoculation, the plants are kept in high humidity conditions at a temperature of 20°–22° C. Thereafter, the plants are kept in ambient glasshouse conditions, that is, in moderate relative humidity and at a temperature of 20° C.

The disease is assessed 10 days after inoculation on the basis of the percentage of the plant covered by sporulating pustules compared with that on the control plants.

(i) Antisporulant Activity against Vine Downy Mildew (*Plasmopara viticola*; Pva)

The test is a direct antisporulant one using a foliar spray. The lower surfaces of leaves of whole vine plants (cv Cabernet Sauvignon) are inoculated by spraying with an aqueous suspension containing $10^4$ zoosporangia/ml 2 days prior to treatment with the test compound. The inoculated plants are kept for 24 hours in a high humidity compartment, and then 24 hours at glasshouse ambient temperature and humidity. When the plants are dry, infected leaves are sprayed on their lower surfaces with a solution of active material in 1:1 water/acetone containing 0.04% w/w "Triton X-155" (trade mark) (an octylphenol polyethoxylate surfactant). The spraying is carried out with a moving track sprayer with delivers 620 liter/ha, and the concentration of active material is calculated to give an application rate of 1 kg/ha. After spraying, the plants are returned to normal glasshouse conditions for 96 hours and are then transferred to the high humidity compartment for 24 hours to induce sporulation, prior to assessment. Assessment is visual and is based on the percentage of the leaf area covered by sporulation compared with that on control leaves.

(j) Activity against Rice Leaf Blast (*Pyricularia oryzae*; Po)

The test is a direct eradicant one using a foliar spray. The leaves of rice seedlings (about 30 seedlings per pot) are sprayed with an aqueous suspension containing $10^5$ spores/ml 20–24 hours prior to treatment with the test compound. The inoculated plants are kept overnight in high humidity and then allowed to dry before spraying at a dosage of 1 kg of active material per hectare using a track sprayer as described under (a). After treatment the plants are kept in a rice compartment at 25°–30° C. and high humidity. Assessments are made 4–5 days after treatment and are based on the density of necrotic lesions and the degree of withering when compared with control plants.

The extent of disease control in all the above tests is expressed as a rating compared with either an untreated control or a diluent-sprayed-control, according to the criteria:

0 = less than 50% disease control,
1 = about 50-80% disease control, and
2 = greater than 80% disease control.

The results of the above tests are given in Table 3 below.

TABLE 3

| Ex. No. | Pvp | Bcp | Ph | Fs | Ln | Eg | As | Pr | Pva | Po |
|---------|-----|-----|----|----|----|----|----|----|-----|-----|
| 1 | 1 | | 1 | | | 2 | | -2 | | 1 |
| 2 | | | | 1 | | 2 | | 2 | 2 | 1 |
| 3 | 2 | | 2 | 1 | 1 | | | 1 | 1 | |
| 4 | 2 | 2 | 2 | 2 | | 2 | | | 2 | 2 |
| 5 | 1 | 2 | 2 | 2 | | 2 | | 2 | 2 | 2 |
| 6 | | | | 1 | | 1 | | 2 | | |
| 7 | 1 | | 2 | 2 | | 1 | | | 2 | |
| 8 | 2 | | 2 | 2 | 1 | 2 | 1 | | | |
| 9 | | | | 1 | | | | | | |
| 10 | 1 | | | 2 | | 2 | | | 1 | 2 |
| 11 | 2 | 2 | 1 | | | 2 | | 2 | 2 | |
| 12 | | | 1 | | | | | | | |
| 13 | 2 | | | 1 | | | | 2 | | |
| 14 | 2 | | 1 | 1 | 1 | 2 | | 2 | 2 | |

The fungicidal activity of certain of the compounds was investigated further, in secondary screening. These revealed that certain compounds were found to have particularly high activity against certain fungi. In particular, Example 4 was found to have especially interesting activity against vine downy mildew and rice leaf blast.

Certain of the compounds were shown in tests to have nematicidal acticity.

We claim:

1. A fungicidal composition which comprises a carrier and, as active ingredient, a compound of the formula:

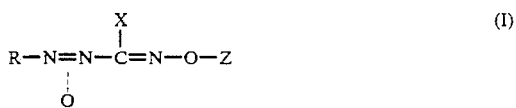

where R represents an optionally substituted aryl group; X represents a hydrogen atom or an amino group or an optionally substituted alkyl, aryl, or thienyl group, and Z represents a hydrogen atom or alkanoyl group.

2. The composition of claim 1, wherein R is selected from the group consisting of phenyl or a halogen-substituted phenyl group.

3. The composition of claim 1, wherein X is selected from the group consisting of a hydrogen atom, an optionally substituted alkyl or phenyl group, or a thienyl group.

4. The composition of claim 3, wherein X is selected from the group consisting of a hydrogen atom, an alkyl or phenyl group.

5. The composition of claim 1, wherein Z represents a hydrogen atom.

6. The method of combating a fungus at a locus, which comprises treating the locus with a fungicidally effective amount of a compound of formula I, as defined in claim 1.

7. A method of combating a fungus at a locus, which method comprises treating the locus with a fungicidally effective amount of a composition as claimed in claim 1.

* * * * *